United States Patent [19]
Osemwota

[11] Patent Number: 5,833,602
[45] Date of Patent: Nov. 10, 1998

[54] PROCESS OF CONTINUOUS NONINVASIVE HEMOMETRY

[76] Inventor: Omoigui Osemwota, 1520 Manhatton Beach Blvd., Manhatton Beach, Calif. 90266

[21] Appl. No.: 327,361

[22] Filed: Oct. 11, 1994

Related U.S. Application Data

[63] Continuation-in-part of Ser. No. 123,682, Sep. 20, 1993, abandoned.

[51] Int. Cl.$^6$ ..................................................... A61B 5/00
[52] U.S. Cl. ........................................... 600/310; 600/322
[58] Field of Search ............................... 600/310, 322–4, 600/326, 328, 330, 331; 356/41

[56] References Cited

U.S. PATENT DOCUMENTS

| | | | |
|---|---|---|---|
| 4,883,055 | 11/1989 | Merrick | 128/633 |
| 4,927,264 | 5/1990 | Shiga et al. | 128/633 |
| 5,111,817 | 5/1992 | Clark et al. | 128/633 |

*Primary Examiner*—Robert L. Nasser

[57] ABSTRACT

This invention relates to a process of determining continuously and non-invasively (without the withdrawal of blood.) the concentrations of hemoglobin. This is done by measurement of the path length and analysis of the pulsatile component of absorbance of multiple wave lengths of light transmitted through a tissue bed. This invention also relates to the process of simultaneous direct or indirect measurement of the pulsatile arterial width or arterial diameter which is equivalent to the pulsatile path length of the light transmitted across the tissue bed. Measurement of this arterial diameter or pulsatile path length is a prerequisite for non invasive determination of the hemoglobin, hematocrit or pigment concentrations in blood.

2 Claims, 9 Drawing Sheets

Figure 9

Comparison between different diameter-pressure relationships proposed in the literature: (1) Langewouters et al 1984, (2) van Loon et al 1977, (3) Vander Werff 1974, (4) Powalowski and Pensko 1985, (5) Kivity and Collins 1974 (6) Hayashi et al 1980. The residual mean square of the regression is calculated for one measurement of each five healthy subjects. The mean value for the group is reported in the last column.

| Fitted model | Residual Mean Square × $10^{-6}$ | | | | | |
|---|---|---|---|---|---|---|
| | Subject no. | | | | | Mean |
| | 1 | 2 | 3 | 4 | 5 | |
| (1) $S = a_1 \left[ \frac{\pi}{2} + \tan^{-1}\left(\frac{p - a_2}{a_3}\right) \right]$ | 4.7 | 3.3 | 2.3 | 2.2 | 5.1 | 3.5 |
| (2) $S = a_1 + a_2[1 - \exp(a_3.p)]$ | 4.3 | 3.5 | 2.7 | 3.1 | 5.4 | 3.8 |
| (3) $S = a_1 \left[ 1 + tgh\left(\frac{p}{a_2}\right) \right]$ | 9.2 | 4.7 | 9.9 | 6.3 | 5.6 | 7.1 |
| (4) $p = a_1.\exp(a_2.S)$ | 9.1 | 8.0 | 6.2 | 5.7 | 15.4 | 8.9 |
| (5) $p = a_1.S^3 + \frac{a_2}{S}$ | 5.7 | 7.2 | 11.9 | 5.1 | 16.5 | 9.3 |
| (6) $p = a_1.\exp(a_2.D)$ | 18.3 | 9.1 | 18.3 | 13.1 | 16.4 | 15.0 |

1. Langewouters G.J, Wesseling K.H. and Goedhard W.J.A. 1984: The static elastic properties of 45 human thoracic and 20 abdominal aortas in vitro and the parameters of a new model: J. Biomech. 17 425-35
2. van Loon P, Klip W and Bradley EL 1977: Length-force and volume-pressure relationships of arteries: Biorheology 14: 181-201
3. Vander Werff T.J. 1974: Significant parameters in arterial pressure and velocity development: J. Biomech. 7: 437-47
4. Powaloski T and Pensko B. 1985: A non-invasive ultrasonic method for the blood flow and pressure measurements to evaluate the hemodynamic properties of the cerebro-vascular system. Arch. Acoust. 10: 303-14
5. Kivity Y and Collins R. 1974 Non linear wave propagations in visco-elastic tubes: applications to aortic rupture: J. Biomech. 7: 67-76
6. Hayashi K, Handa H, Nagasawa S and Okumura A 1980 Stiffness and elastic behaviour of human intracranial and extracranial arteries: J. Biomech. 13 175-84

Typical RF echo signal from the anterior and posterior arterial walls.

PROCESS OF CONTINUOUS NONINVASIVE HEMOMETRY

This application is a continuation-in-part of the application entitled PROCESS OF CONTINUOUS NONINVASIVE HEMOGLOBINOMETRY, Ser. No. 08/123,682, filed on Sep. 20, 1993.

BACKGROUND OF THE INVENTION

This invention relates to a process by which existing technology may be used by a health care provider in continuously measuring the hemoglobin and hematocrit concentrations in a patients blood. This is done non-invasively by analysis of the pulsatile component of absorbance of selected wave lengths of light transmitted through a tissue bed. Devices using the process of hemometry will enable continuous measurement of hemoglobin and hematocrit without the withdrawal of blood. Patients will no longer have to be subjected to the pain and trauma of repeated withdrawal of blood. Over and under-transfusions will be avoided by continuous non-invasive trending of the hemoglobin and hematocrit. By not having to repeatedly withdraw blood with a needle and syringe, health care providers will be spared the risks of blood transmitted bacterial and viral infections.

DESCRIPTION OF THE PRIOR ART

The hemoglobin and hematocrit concentration is a measure of the amount of red blood cells in the human body. The proper functioning of the body is dependent on adequate amounts of red blood cells. Hemoglobin and hematocrit measurements are the most frequently performed medical laboratory tests. At present, these require withdrawal of a sample of blood by needle stick or puncture. The sample of blood is then analyzed by a laboratory oximeter and the hemoglobin concentration determined based on curent methods of oximetry.

When light passes through matter, it is transmitted, absorbed, or reflected. The Lambert-Bear Law, on which current methods of oximetry are based, govern this phenomenon according to the following:

Law 1.: The intensity of light transmitted through a solution is related to the concentration of a solute in suspension.

Equation: $I_{trans} = I_{in} - (DC@)$ where $I_{trans}$ = intensity of transmitted light
$I_{in}$ = intensity of incident light
D = distance light is transmitted through the liquid
C = concentration of solute (hemoglobin)
@ = extinction coefficient of the solute a constant for a given solute at a specific wavelength).
Extinction is the light absorption of a unit concentration and path length of a substance.

SUMMARY OF THE INVENTION

In FIG. 1, the concentration of a solute dissolved in a solvent can be calculated from the logarithmic relationship between the incident and transmitted light intensity and the solute concentration.

Law 2: The total absorption of a system of absorbers is the sum of their independent absorbances.

$$A\ total = E1C1L1 = E2C2L2 + \ldots EnCnLn$$

where A total is the absorbance of a mixture of substances at a specific wavelength
E1 is the extinction of a substance 1 at wavelength n
C1 is the concentration of substance 1
L1 is the path length of the light through substance 1 at wavelength n
E2 is the extinction of a substance 2 at wavelength n
C2 is the concentration of substance 2
L2 is the path length of the light through substance 2 at wavelength n For Beer's Law to be valid, both the solvent and the container must be transparent at the wavelength used, the light path length must be known exactly and no other absorbing species can be present in the solution. With empirical corrections to its calibrations, these requirements may be fulfilled in laboratory devices, In clinical devices a limiting factor has been the requirement to measure the path length of light noninvasively in living tissue. Laboratory oximeters determine hemoglobin concentration from a sample of blood by spectrophotometry. Using interference filters on an emitted light beam, monochromatic light at four specific wavelengths (535.0, 582.2, 594.5 and 626.5 nm) is produced. The light beam is split with one beam transmitted through a cuvette filled with a solution of lysed blood to a sample photo-detector to generate a sample absorbance. The other beam is imaged through a cuvette filled with a zeroing solution onto a reference photo-detector to generate a blank absorbance. The absorbance of the blood A at each wavelength is represented by the equation:

$$A\ (sample) - A(blank) = A(blood)$$

where A is the absorbance at each wave length

A coefficient matrix is determined by oximeter analysis of 100% content for each of thefour Hemoglobin species (Reduced Hb, Oxygenated Hb, COHb and Meth Hb). Utilizing this matrix, the following equations are solved to determine the concentrations of the four measured Hb species in the blood sample.

Equations:

$$C_{(RHb)} = K(E_{535RHb}A_{535} + E_{585RHb}A_{585} + E_{594RHb}A_{594+} + E_{626RHb}A_{626})$$

$$C_{(O2Hb)} = K(E_{535O2Hb}A_{535} + E_{585O2Hb}A_{585} + E_{594O2Hb}A_{594+} + E_{626O2Hb}A_{626})$$

$$C_{(COHb)} = K(E_{535COHb}A_{535} + E_{585COHb}A_{585} + E_{594COHb}A_{594+} + E_{626COHb}A_{626})$$

$$C_{(MetHb)} = K(E_{535MetHb}A_{535} + E_{585MetHb}A_{585} + E_{594MetHb}A_{594+} + E_{626MetHb}A_{626})$$

where
C = concentration of each Hb species
K = a scalar constant set by the THb calibration procedure
E = each coefficient in the matrix (4 Hb species at 4 wavelengths)
A = the absorbance value of the blood at each wavelength The Total hemoglobin (THb) value (g/dl) is the sum of the four concentrations $$THb = C_{(RHb)} + C_{(O2Hb)} + C_{(COHb)} + C_{(MetHb)}$$

Calibrations are performed using blood samples with known hemoglobin concentrations assayed by laboratory spectrophotometry.

Pulse oximeters analyze the pulsatile component of absorbance and determine continuously and noninvasively hemoglobin oxygen saturation. Pulse oximeters measure the pulsatile component of red (660 nm) and infra-red light (940 nm) absorbance after transmission through a tissue bed (e.g. finger or ear). These wavelengths are used because they maximize the differences in absorbance of deoxy and oxygenated hemoglobin. At the red wavelength of 660 nm, deoxyhemoglobin absorbs approximately 10 times as much light as does oxygenated hemoglobin. At the infra-red wavelength of 940 nm, the absorption coefficient of oxygenated hemoglobin is greater than that of deoxyhemoglobin. The output light at each wavelength consists of two components. The baseline or DC component is a large constant light output level and represents the absorbances of the tissue bed, including venous blood, capillary blood and nonpulsatile arterial blood. The pulse-added, or AC component varies with pulsation of the arterial blood (FIG. 2). The amplitude of both the DC and AC levels are directly dependent on the incident light intensity. Dividing the AC level by the DC level (at each wavelength) gives a corrected AC level (Equation 1) that is no longer a function of the incident intensity. This corrected AC level is a function only of the extinction of the two species of hemoglobin (FIG. 3) and the path length of arterial blood through which the light has passed. The AC light is only a function of arterial blood since essentially only the arterioles are pulsating in the lights path. The transmitted light at each wavelength is converted to an electronic signal by means of a silicone photodiode. The signals are amplified, filtered, converted to digital values by an analog-to-digital converter and then fed into a microprocessor. The oximeter then calculates the ratio R of the pulse added absorbance at 660 nm (AC660) to the pulse added absorbance at 940 nm (AC940). This ratio (Equation 2) is empirically related to the hemoglobin oxygen saturation (SaO2).

Equation 1

$$PAn=ACn/DCn$$

where PAn=Pulsatile absorbance at wavelength n

ACn=AC component at wavelength n

DCn=DC component at wavelength n

Equation 2

$$R=(AC660/DC660)/(AC940/DC940).$$

where R=Ratio of Pulsatile absorbance at wavelength 660 nm and 940 nm

In FIG. 2., is a schematic representation of the absorption of constant intensity light by living tissues. The output light consists of a constant light level with a small amount of modulation caused by the pulsating arterial blood. The constant output light (the DC component) represents all of the non pulsatile absorbers. The pulsatile output light (the AC component) is from the arterial blood which is the only pulsatile component in the series of light absorbers in living tissue.

In FIG. 3, extinction coefficients are plotted against the transmitted light absorbance spectra in the wavelength range of interest (red and infra red range) for four species of hemoglobin. Any point in which two species have the same extinction coefficient is known as the isobestic point. An isobestic point occurs for oxygenated hemoglobin and deoxyhemoglobin at 805 nm.

Calibration curves developed from experimental studies in human volunteers are used to calculate arterial oxygen saturation (SaO2) from the ratio (R) of the light absorbed (A) by the tissue being monitored. In FIG. 4., is a calibration curve used by the oximeter to calculate arterial oxygen saturation (SA02) from the ratio (R) of the light absorbed (A) by the tissue being monitored.

BRIEF DESCRIPTION OF THE DRAWINGS

FIG. 9 is a description of different diameter-pressure relationships proposed in the literature.

Specifically, FIG. 9 shows a comparison between following different diameter-pressure relationships proposed in the literature, with the number of the article corresponding tot he number on the table in FIG. 9:
(1) Langewouters G. J, Wesseling K. G. and Goedhard W. J. A 1984: The static elastic properties of 45 human thoracic and 20 abdominal aortas in vitro and the parameters of a new model, J. Biomech, 17, 425–35;
(2) van loon P., Klip W. and Bradley E.L. 1977, Length-force and volume-pressure relationships of arteries, J. Biorheology 14, 181–201;
(3) Vander werff T. J. 1974, Significant parameters in arterial pressure and velocity development, J. Biomech 7, 437–47;
(4) Powaloski T. and Pensko B., 1985, A non-invasive ultrasonic method for blood flow and pressure measurements to evaluate hemodynamic properties of the cerebrovascular system, Arch. Accoust. 10, 303–14;
(5) Kivity Y. and Collins R. 1974, Non linear wave propagations in visco-elastic tubes: applications to aortic rupture, J. Biomech 7, 67–76; and
(6) Hayashi K., Handa H., Nagasawa S., and Okumura A. 1980, Stiffness and elastic behaviour of human intracranial and extracranial arteries, J. Biomech 13, 175–84.

DETAILED DESCRIPTION

Like the Laboratory oximeter, the continuous noninvasive hemometer will determine hemoglobin concentrations. Unlike the laboratory oximeter, hemoglobin concentrations will be determined continuously and noninvasively by a probe attached to the tissue (e.g. finger) rather than one single measurement from a sample of blood. Unlike the Laboratory oximeter, the hemometer will have to measure noninvasively, variable path lengths of light in order to determine hemoglobin concentrations.

Like the Pulse oximeter measurements will be determined continuously by a probe attached to the tissue (e.g. finger). Unlike the Pulse oximeter, this will determine continuous hemoglobin concentrations in absolute amounts rather than continuous hemoglobin oxygen saturation's derived frrom ratios. Unlike the Pulse oximeter, the hemometer will need to measure the path length of the light through the pulsating artery.

NON INVASIVE MEASUREMENT OF HEMOGLOBIN CONCENTRATION—THE SINGLE WAVELENGTH METHOD THIS REQUIRES THE PATH LENGTH OF LIGHT TO BE MEASURED (SEE BELOW)

Figure 1:
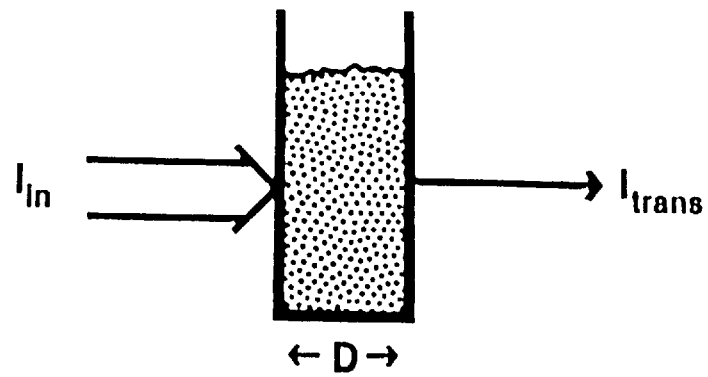
FIG. 1 is a diagram showing a light transmitted through a solute dissolved in a solvent. The concentration of the solute can be calculated from the logarithmic relationship between the incident and transmitted light intensity and the solute concentration.
Figure 2:
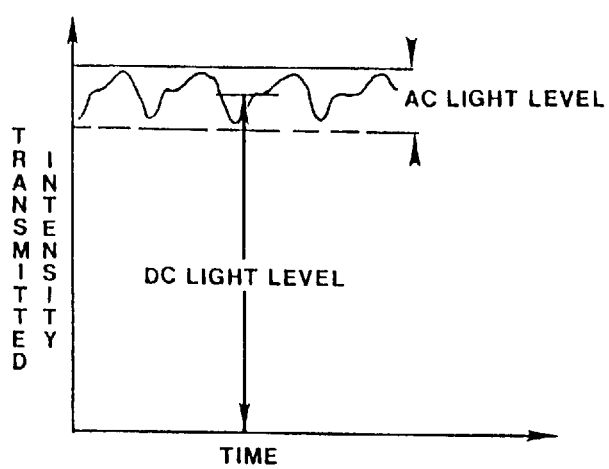
FIG. 2 is a diagram showing the two components of a transmitted wavelength of light. The baseline or DC component is a large constant light output level and represents the absorbances of the tissue bed, including venous blood, capillary blood and nonpulsatile arterial blood. The pulse-added, or AC component varies with pulsation of the arterial blood. The amplitude of both the DC and AC levels are directly dependent on the incident light intensity.
Figure 3:
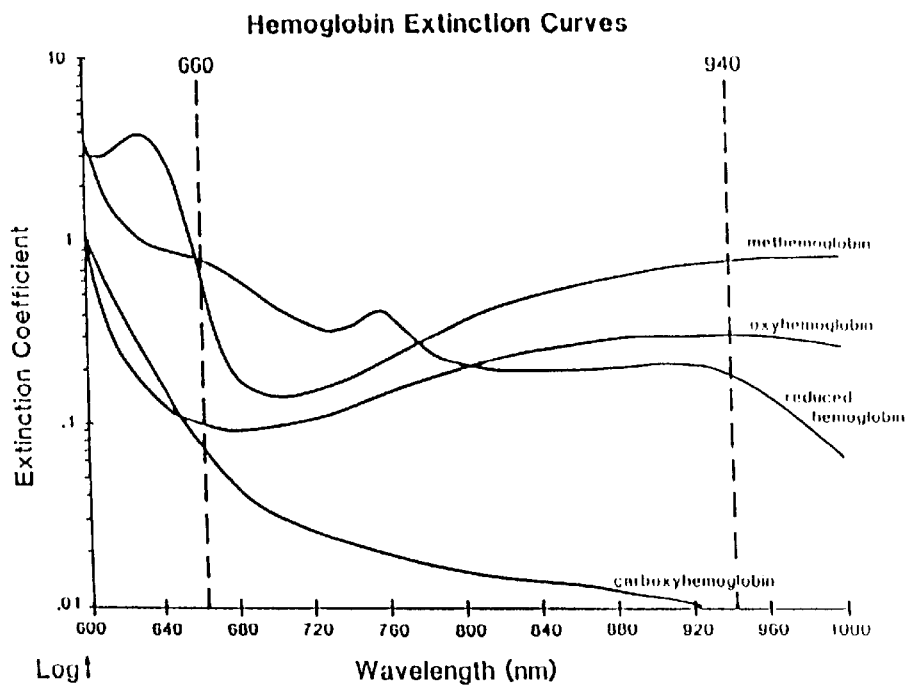
FIG. 3 is a diagram showing extinction coefficients plotted against the transmitted light absorbance spectra in the wavelength range of interest (red and infra red range) for four species of hemoglobin. Any point in which two species have the same extinction coefficient is known as the isobestic point. An isobestic point occurs for oxygenated hemoglobin and deoxyhemoglobin at 805 nm.
Figure 4:
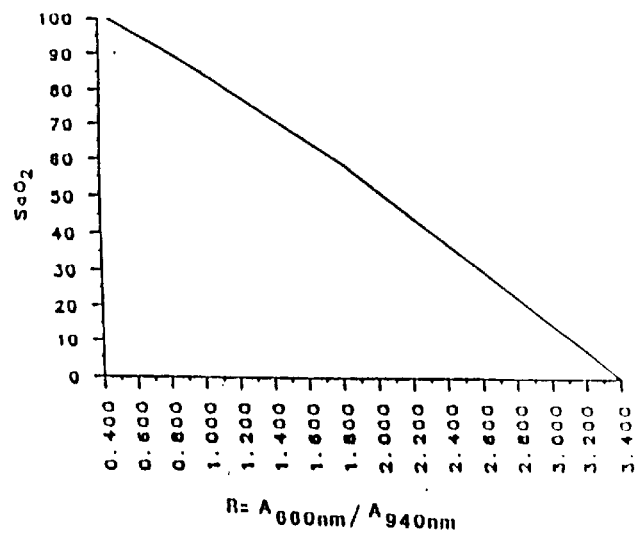
FIG. 4 is a calibration curve used by an oximeter to calculate arterial oxygen saturation (SAO2) from the ratio (R) of the two wavelengths of light absorbed (A660 nm and A940 nm) by the tissue being monitored.
Figure 5:
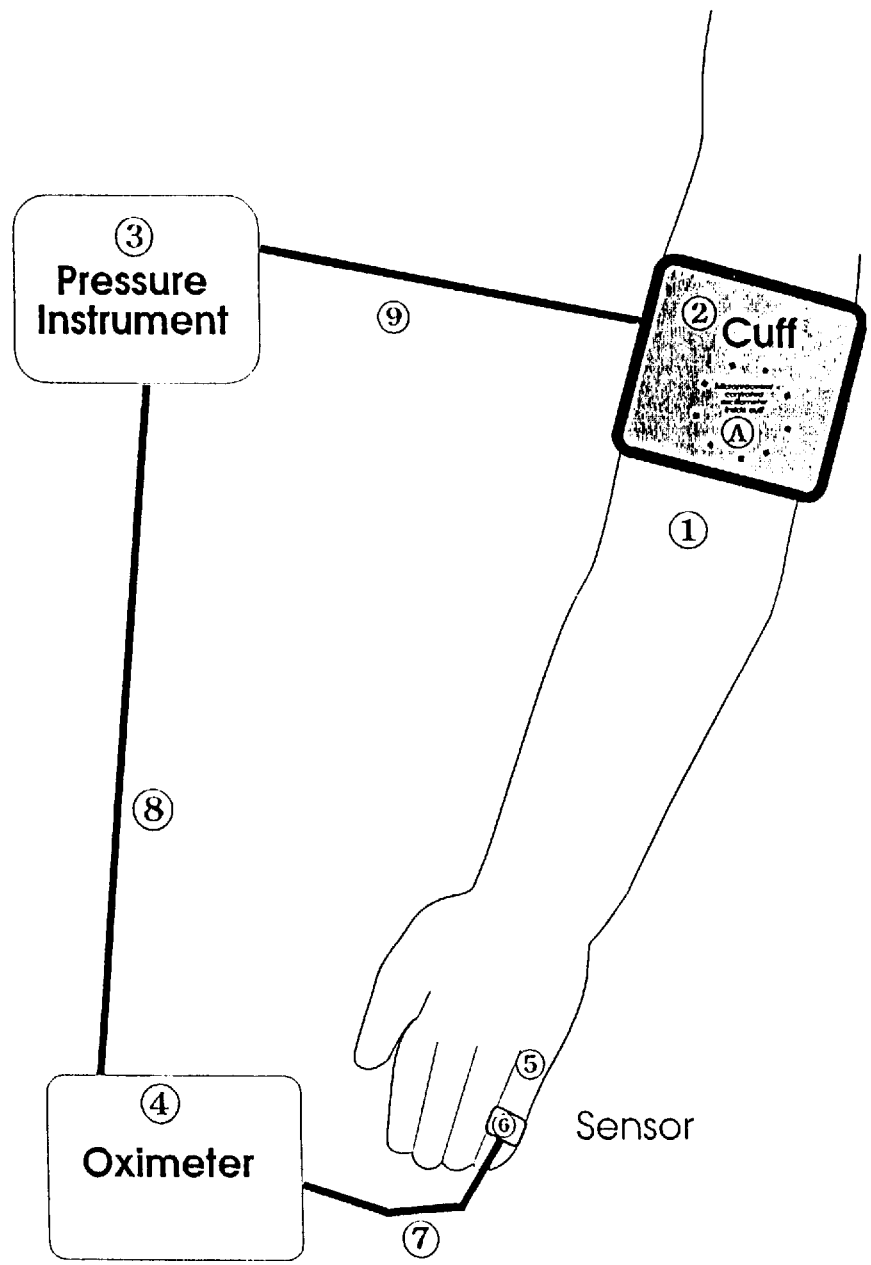
FIG. 5 is a diagram of the apparatus used to carry out the process. A pressure cuff (2) with a microprocessor controlled oscillotonometer (A) is attached to the arm of the patient. A sensor probe (6) from the single to four wavelength oximeter (4) is attached to a finger (5) of the patient on the same arm. Light from the pulse oximeter sensor is transmitted across the finger. The oximeter (4) communicates with the pressure instrument (3) through a communication link (8).

At a wavelength of 805 nm (the isobestic point), the optical extinction coefficient of reduced and oxygenated hemoglobin are the same (FIG. 3). The hemometer would measure the pulsatile absorbance (PA=AC/DC) of this wavelength of light after transmission through a tissue bed (e.g. finger). Use of the pulsatile absorbance takes into account the effect of absorption of light by skin, soft tissue, venous and capillary blood. Use of the isobestic wavelength ensures that the absorption of light is independent of the degree of oxygenation of the blood. The pulse added absorbance at the isobestic wavelength will thus be directly related to the concentration of oxygenated and deoxyhemoglobin irrespective of their saturation or oxygen content. The Concentration of oxygenated hemoglobin (C1) and deoxyhemoglobin (C2)) may be derived as follows:

Beer's Law 2 relates absorbance (A) to extinction coefficient En and path length Ln at wavelength n $$A = E_n C_n L_n$$

Extrapolating Beer's Law with the use of pulsatile absorbance (PAn) in which path length is measured (see page 9), the modified equation is:

$$PA_n = E_n C_n L_n$$

and $C_n = PA_n / E_n L_n$

The sum of the concentration (C1+C2) of oxygenated and deoxyhemoglobin is obtained at the isobestic wavelength of 805 nm Therefore $C1 + C2 = @PA805/E805 L_n 805$ Now $PA805 = AC805/DC805$ Thus $C1 + C2 = @AC805/DC805 E805 L_n 805$ where
AC=absorbance of tissue bed including venous blood
DC=absorbance of pulsatile arterial blood
PA=Pulsatile Absorbance at a wavelength of 805 nm
C1=Concentration of oxygenated hemoglobin
C2=Concentration of deoxyhemoglobin
@=scalar coefficient
E805=extinction coefficient at a wavelength of 805 nm
Ln805=is the path length of the light at a wavelength of 805 nm The scalar coefficient @ will be determined by Calibration curves from experimental studies in human volunteers (plotting PA/E805 against known hemoglobin concentrations determined by laboratory spectrophotometry).

In the absence of COHb and MetHb or their presence in negligible amounts:

$$Total\ Hb = C1 + C2 = @PA/E805 L_n 805$$

Other derivatives that may be calculated from Total Hb (THb) are:
1. Hematocrit (HCT)

$$HCT = THb \times 3$$

substituting for THb $$HCT = @PA/E805 L_n 805 \times 3$$

2. Arterial Oxygen Content (CA02)

$$CAO2\ (vol\%\ O2) = 1.39 \times THb \times \%O2Hb/100$$

substituting for THb $$CAO2(vol\%\ O2) = 1.39 \times @PA/E805 L_n 805 \times \%O2Hb/100$$

THREE METHODS TO MEASURE THE PATHLENGTH OF LIGHT THROUGH A PULSATING ARTERY (OR THE PULSATING WIDTH OF THE ARTERY)

Measurement of the pathlength of light through a pulsating artery (or the pulsatile width) is based on the following laws;

OMOIGUI'S LAW 1: The pathlength of light through a pulsating artery (or the pulsatile width) is equivalent to the pulsating distance of the artery which is equivalent to the maximal arterial diameter.

OMOIGUI'S LAW 2: The maximal arterial diameter due to pulsation of the arterial wall is a function of the distending pressure on the arterial wall which is measured as the systolic arterial pressure.

The maximal arterial diameter may be derived from the systolic arterial pressure by statistical analysis and non linear regression of the arterial diameter and arterial pressure curves. Values to plot these curves are obtained by measuring simultaneously at the same site, the arterial diameter and arterial pressure of an artery.

MEASUREMENT OF PATHLENGTH OF LIGHT (ARTERAL DIAMETER) AND HEMOGLOBIN CONCENTRATION—METHOD 1

The relationship between arterial pressure and arterial diameter (pulsating width) may be characterized by measuring simultaneously at the same site, the arterial diameter and arterial pressure of an artery in a large number of human volunteers of various ages. Such measurements may be obtained by utilizing synchronized ultrasonic (e.g. Asulab SA) and photoplethysmographic (e.g. Finapres™) devices. Statistical analysis and non linear regression of the arterial diameter against arterial pressure curves derived from these actual measurements will determine the relationship. The arterial pressure-diameter relationship has been described by several non-linear mathematical expressions (FIG. 9)[1,2,3,4] some of which utilize pressure-diameter equations (arctangent function and three optimal fit parameters) in the form:

$$S = \pi d^2/4 = á[\pi/2 + \tan^{-1}(p - \beta/\ddot{y})]$$

Therefore:

$$d = 2\sqrt{[á^{-1}/2 + á/\pi \tan(p - \beta/\ddot{y})]}$$

where:

S=arterial cross-sectional area d=arterial diameter

á=optimal fit parameter characterizing the arterial diameter-pressure curve.

β=optimal fit parameter characterizing the arterial diameter-pressure curve.

ÿ=optimal fit parameter characterizing the arterial diameter-pressure curve.

[1] van Loon P., Klip W. and Bradley E.L. 1977: Length-force and volume-pressure relationships of arteries: Biorheology 14: 181–201
[2] Vander Werff T. J. 1974: Significant parameters in arterial pressure and velocity development: J. Biomech. 7:437–47
[3] Tardy Y., Meister J. J. et al: Non invasive estimate of the mechanical properties of peripheral arteries from ultrasonic and photoplethysmographic measurements: Clin. Phys. Physiol. Meas., 1991, Vol 12, No 1, 39–54.
[4] Langewouters G. J. Wesseling K. H. and Goedhard W. J. A. 1984: The static elastic properties of 45 human thoracic and 20 abdominal aortas in vitro and the parameters of a new model: J. Biomech. 17 425–35

To measure the pulsatile pathlength of light which is equivalent to the pulsatile arterial width or maximal arterial diameter, it will be necessary to determine the systolic arterial pressure of the artery adjacent or at the site of the pulse oximeter sensor.

Figure 6:
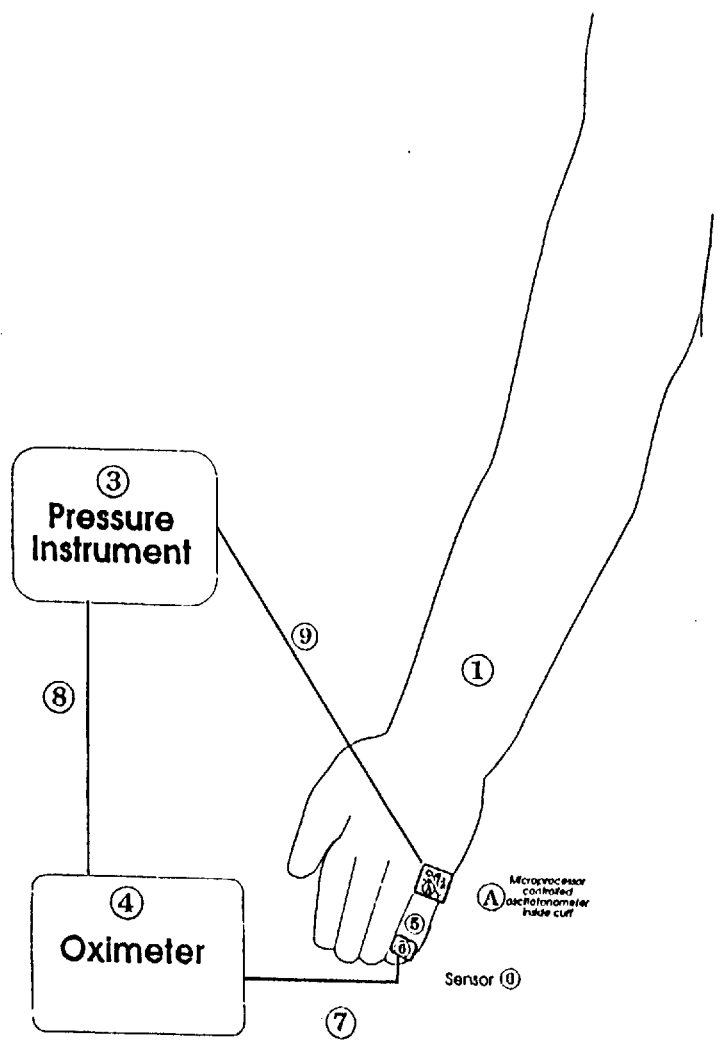
FIG. 6 is another diagram of the same apparatus used to carry out the process. However the pressure cuff (2) with a microprocessor controlled oscillotonometer (A) is attached to the arm of the patient. A sensor probe (6) from the single to four wavelength oximeter (4) is attached to said finger of the patient on the same arm. Light (5) from the pulse oximeter sensor is transmitted across the finger. The oximeter (4) communicates with the pressure instrument (3) through a communication link (8).

In order to carry out the above described processes (FIG. 6), a pressure cuff (2) for an automatic oscillometric blood pressure instrument (3) with a microprocessor controlled oscillotonometer (A) is attached to the arm or finger of the patient. A sensor probe (6) from the single to four wavelength oximeter (4) is attached to said finger (5) of the patient on the same arm. The cuff pressure is first increased above the expected systolic blood pressure value, then it is slowly and automatically decreased while pressure oscillations in the cuff are measured electronically by the microprocessor controlled oscillotonometer (A) and systolic blood pressures are determined. The process will be done continuously with deflation and reinflation of the cuff to determine the maximum systolic arterial pressure. The maximal arterial diameter (pulsatile width) will be calculated using an arterial pressure diameter equation (see FIG. 9), such as $$S=\Sigma d^2/4=a[\Sigma/2+\tan^{-1}(p-\beta/\ddot{y})]$$

where:

S=arterial cross-sectional area d=arterial diameter a=optimal fit parameter characterizing the arterial diameter curve β=optimal fit parameter characterizing the arterial diameter curve y=optimal fit parameter characterizing the arterial diameter curve p=pressure The oximeter (4) communicates with the automatic oscillometric blood pressure device (3) through a communication link p=pressure (8) and light from the pulse oximeter sensor is transmitted across the finger during deflation of the cuff. The absorbance of the isobestic wavelength of light transmitted through the pulsating artery will be determined by the amount of light detected by the sensor probe on the opposite side of the finger. The pulse added absorbance at the isobestic wavelength will be directly related to the concentration of oxygenated and deoxyhemoglobin irrespective of their saturation or oxygen content. The Concentration of each species of hemoglobin (Chb) will be empirically determined using the equations described above. A correction coefficient k is determined by plotting derived hemoglobin concentrations with known hemoglobin concentrations in human volunteers of various ages will then be determined below.

MEASUREMENT OF PATHLENGTH OF LIGHT AND HEMOGLOBIN CONCENTRATION— METHOD 2

Figure 11:
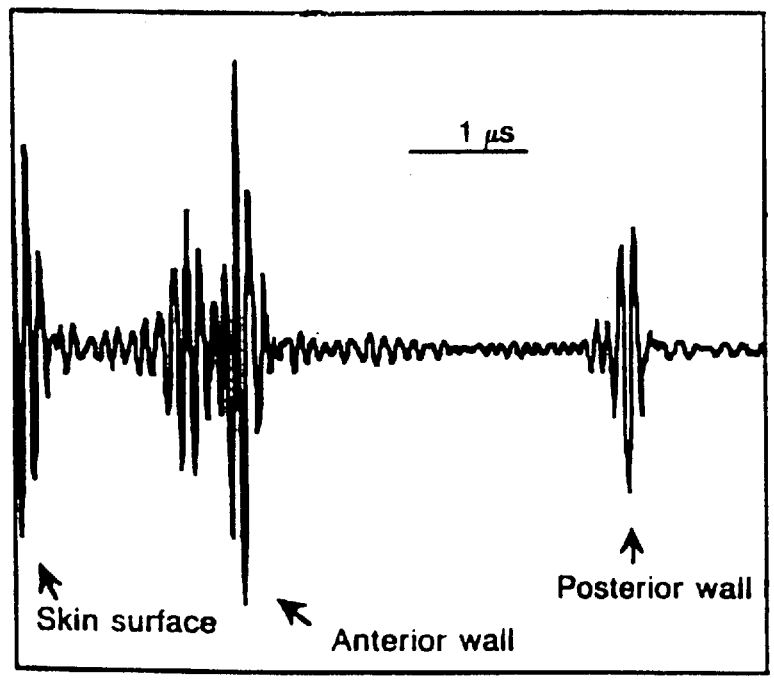
FIG. 11 is an example of an ultra sound echo reflected from the anterior and posterior walls of an artery.

Measurement of the pathlength of light through a pulsating artery (or the pulsatile width/diameter of the artery) may occur by use of an ultrasonic echo tracking device (or pulsed doppler ultrasound) that allows continous non-invasive recording of the internal diameter of peripheral arteries. Short ultrasonic pulses are generated and detected by a piezoelectric transducer. The timed displacement of the signal waveform (echo) reflected by the interface between blood and the inner and outer arterial walls and identified on an RF mode display corresponds to the arterial diameter (FIG. 11). The maximum difference between the two waveforms is proportional to the maximal arterial diameter which is equivalent to the pulsatile arterial width of the arterial wall.

Figure 7:
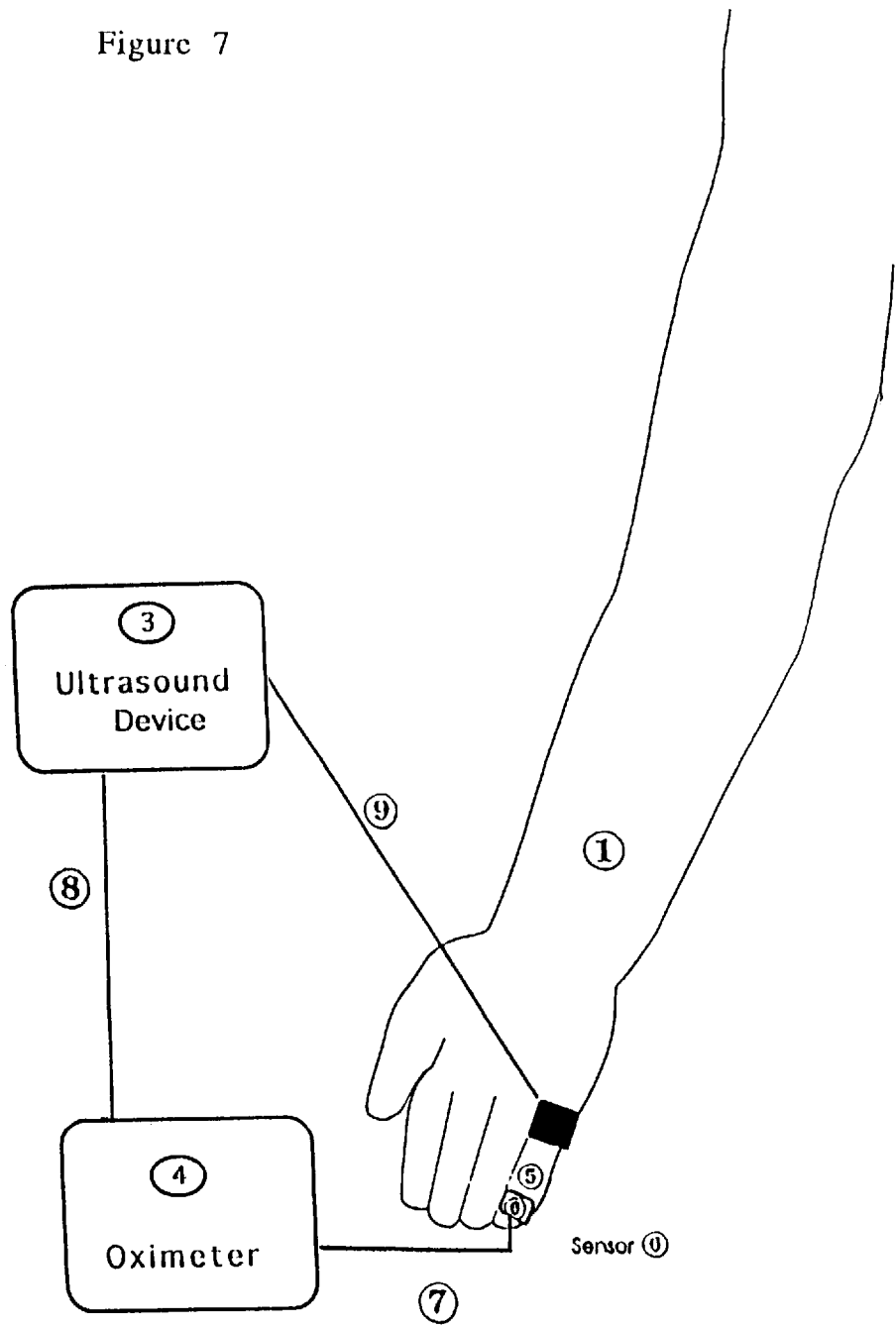
FIG. 7 is a diagram of the second apparatus used to carry out the process. An ultrasound device (13) is attached to the arm of the patient. A sensor probe (6) from the single to four wavelength oximeter (4) is attached to said finger (5) of the patient on the same arm. Light from the pulse oximeter sensor is transmitted across the finger. The oximeter (4) communicates with the ultrasound device (13) through a communication link (8).
Figure 8:
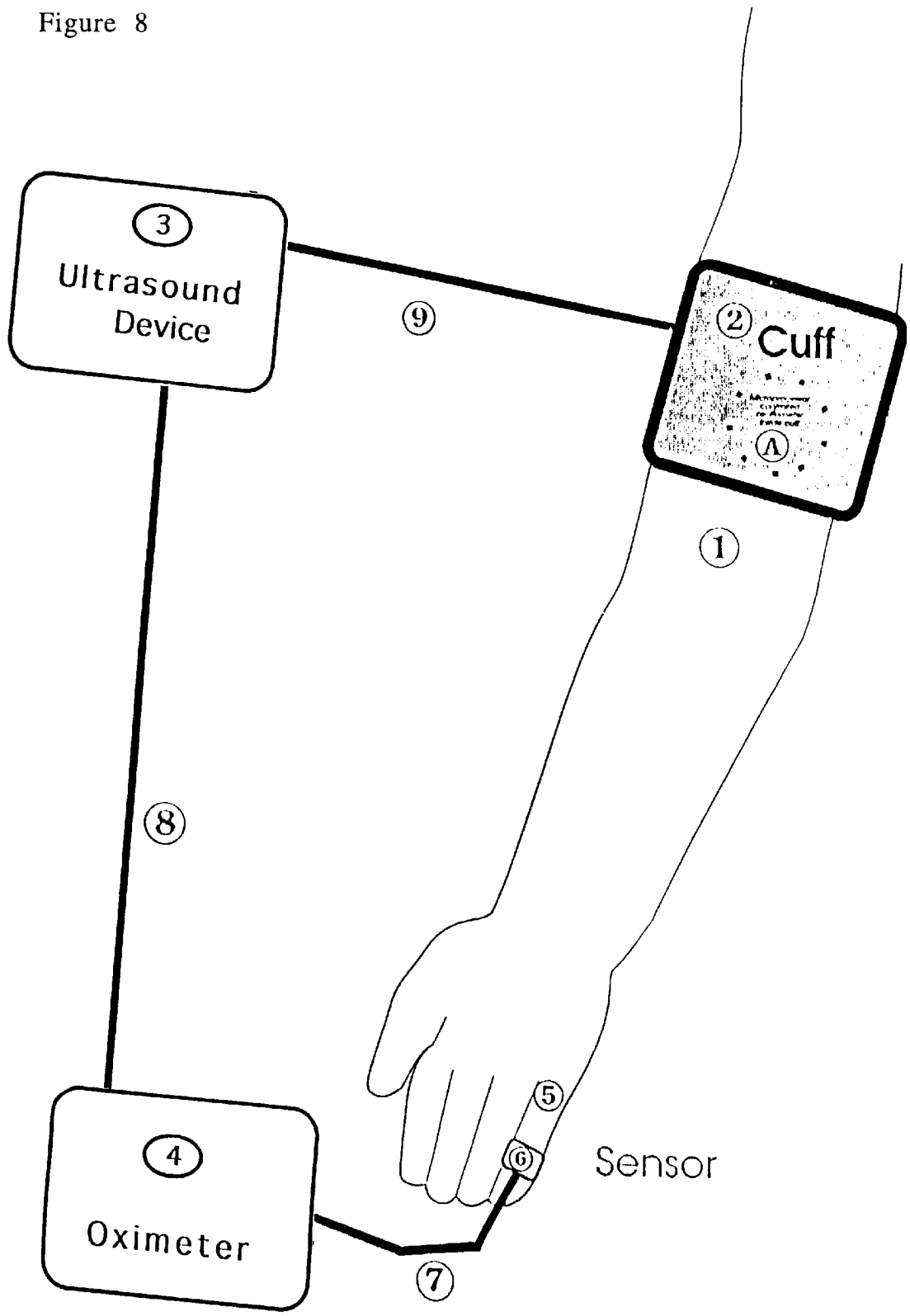
FIG. 8 is another diagram of the second apparatus used to carry out the process. The ultrasound device (3) is attached to the arm of the patient. A sensor probe (6) from the single to four wavelength oximeter (4) is attached to a finger (5) of the patient on the same arm. Light from the pulse oximeter sensor is transmitted across the finger. The oximeter (4) communicates with the ultrasound device (3) through a communication link (8).
Figure 10:
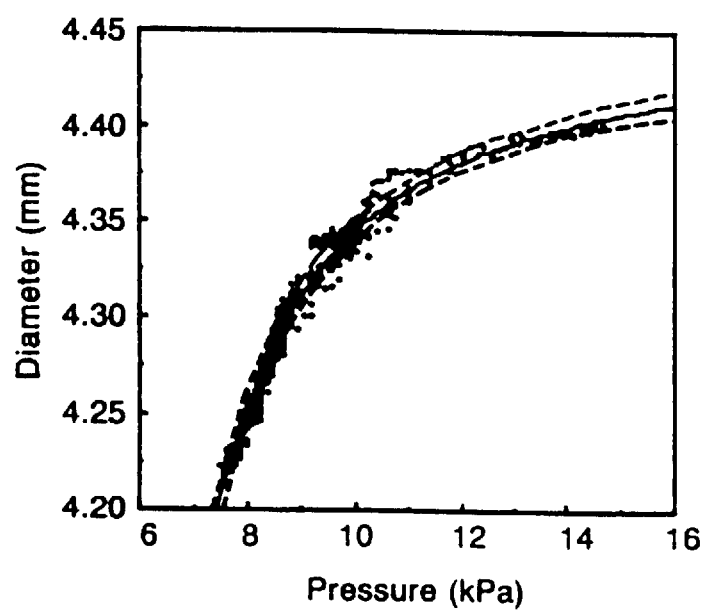
FIG. 10 is a model of an arterial diameter-pressure curve.

In order to carry out the above described processes (FIG. 7, 8), an ultrasonic echo tracking device (13) is attached to the arm or finger of the patient. A sensor probe (6) from the single to four wavelength oximeter (4) is attached to said finger (5) of the patient on the same arm. The arterial diameter will be determined by the ultrasonic echo tracking device (13). The oximeter (4) communicates with the ultrasonic echo tracking device (13) through a communication link (8). The ultrasonic echo tracking device (13) and pulse oximeter sensor (6) are synchronized to enable simultaneous measurements of arterial diameter and pulsatile absorbances respectively. Light from the pulse oximeter sensor is transmitted across the finger simultaneous with generation of short ultrasonic pulses by the ultrasonic echo tracking device (13). The diameter of the pulsating artery will be determined by the ultrasonic echo tracking device (13). The absorbance of the isobestic wavelength of light transmitted through the pulsating artery will be determined by the amount of light detected by the sensor probe on the opposite side of the finger. The pulse added absorbance at the isobestic wavelength will be directly related to the concentration of oxygenated and deoxyhemoglobin irrespective of their saturation or oxygen content. The Concentration of each species of hemoglobin (Chb) will be empirically determined using the equations described above. A correction coefficient k is determined by plotting derived hemoglobin concentrations with known hemoglobin concentrations in human volunteers of various ages.

NON INVASIVE MEASUREMENT OF HEMOGLOBIN CONCENTRATION, HEMOGLOBIN SPECIES CONCENTRATION AND BLOOD PIGMENT CONCENTRATION—MULTIPLE WAVELENGTHS METHOD THIS REQUIRES THE PATH LENGTH OF LIGHT TO BE MEASURED (SEE ABOVE)

According to Beer's Law, at least n wavelengths are required to identify any one absorber of light out of a system of n absorbers. To determine the concentrations of all or any of the species of hemoglobin, the hemometer will measure the pulsatile absorbance of four hemoglobin species at four wavelengths. At each wavelength, the extinction coefficient for one of the species is optimal (e.g. 940 nm for oxygenated hemoglobin, 660 nm for deoxyhemoglobin, 535 nm for carboxyhemoglobin and 626.6 nm for methemoglobin). The pulsatile absorbance at each of the selected wavelengths will be a function of the concentration of the species of hemoglobin. Four linear equations of absorbance are solved simultaneously for four independent variables. The path length of light will be determined as measured above. The Concentration of each species of hemoglobin (Chb) will be empirically determined by the equation:

$$AC/DC=PA$$

$$C(RHb)=@(PA535RHb/E535L535+PA585RHb/E585L585+PA594RHb/E594L594+PA626RHb/E626L626)$$

$$C(O2Hb)=@(PA535O2Hb/E535L535+PA585O2Hb/E585L585+PA594O2Hb/E594L594+PA626O2Hb/E626L626)$$

$$C(COHb)=@(PA535COHb/E535L535+PA585COHb/E585L585+PA594COHb/E594L594+PA626COHb/E626L626)$$

$$C(MetHb)=@(PA535MetHb/E535L535+PA585MetHb/E585L585+PA594MetHbE594L594+PA626MetHb/E626L626)$$

where AC=absorbance of tissue bed including venous blood
   DC=absorbance of pulsatile arterial blood
   PA=Pulsatile Absorbance
   Chb=concentration of hemoglobin species
   @=scalar coefficient
   En=extinction coefficient at wavelength n
   Ln=pathlength of light at wavelength n The scalar coefficient @ will be determined by Calibration curves from experimental studies in human volunteers (plotting PA/EnLn against known concentrations of the hemoglobin species as determined by laboratory spectrophotometry).

$$Total\ Hb=C1+C2+C3+C4$$

where C1=concentration of oxygenated hemoglobin
   C2=concentration of deoxyhemoglobin
   C3=concentration of carboxyhemoglobin
   C4=concentration of methemoglobin
If C3+C4 are negligible $$Total\ Hb=C1+C2$$

C2 (the concentration of reduced or unoxygenated hemoglobin) may also be derived as a function of the oxygen saturation and the concentration C1 of oxygenated hemoglobin.

$$C2=K(SaO2)C1$$

where K is a coefficient derived by Calibration curves from experimental studies in human volunteers plotting known oxygen saturations at known concentrations of oxygenated hemoglobin against known concentrations of deoxyhemoglobin as determined by laboratory spectrophotometry Thus $$Total\ Hb=C1+KSaO2C1$$

As derived previously $$C1=@PA/E940L940$$

where PA=Pulsatile Absorbance
   C1=concentration of oxygenated hemoglobin
   @=scalar coefficient
   En=extinction coefficient at wavelength 940 nm (selected for oxygenated hemoglobin)
   L940=pathlength of light at wavelength 940 nm
Therefore $$Total\ Hb=@PA/E940Ln940+KSaO2@PA/E940L940$$

The multiple wavelength method may also be used to determine the concentration of any hemoglobin species or blood pigment e.g. bilirubin. An additional equation using the optimal wavelength of absorbance for the blood pigment (e.g. 450 nm for bilirubin) will be added to the four equations for the four species of hemoglobin. The pulsatile absorbance of the blood pigment and the four hemoglobin species at five wavelengths will be determined. Five linear equations of absorbance are solved simultaneously for five independent variables. Using the measured path length of light the concentration of the blood pigment and each species of hemoglobin will be determined by solving the equations:

$$C(Bil)=@(PA450Bil/E450L450+PA535Bil/E535L535+PA585Bil/E585L585+PA594Bil/E594L594+PA626Bil/E626L626)$$

$$C(RHb)=@(PA450RHb/E450L450+PA535RHb/E535L535+PA585RHb/E585L585+PA594RHb/E594L594+PA626RHb/E626L626)$$

$$C(O2Hb)=@(PA450O2Hb/E450L450+PA535O2Hb/E535L535+PA585O2Hb/E585L585+PA594O2Hb/E594L594+PA626O2Hb/E626L626)$$

$$C(COHb)=@(PA450COHb/E450L450+PA535COHb/E535L535+PA585COHb/E585L585+PA594COHb/E594L594+PA626COHb/E626L626)$$

$$C(MetHb)=@(PA450MetHb/E450L450+PA535MetHb/E535L535+PA585MetHb/E585L585+PA594MetHb/E594L594+PA626MetHb/E626L626)$$

where AC=absorbance of tissue bed including venous blood

DC=absorbance of pulsatile arterial blood
PA=Pulsatile Absorbance
Cbil=concentration of bilirubin
Chb=concentration of hemoglobin species
@=scalar coefficient
En=extinction coefficient at wavelength n
Ln=pathlength of light at wavelength n The scalar coefficient @ will be determined by Calibration curves from experimental studies in human volunteers (plotting PA/EnLn against known concentrations of bilirubin and the four hemoglobin species as determined by laboratory spectrophotometry).

$$Total\ Hb = C1 + C2 + C3 + C4$$

where C1=concentration of oxygenated hemoglobin
C2=concentration of deoxyhemoglobin
C3=concentration of carboxyhemoglobin
C4=concentration of methemoglobin
If C3+C4 are negligible $$Total\ Hb = C1 + C2$$

C2 (the concentration of reduced or unoxygenated hemoglobin) may be derived as a function of the oxygen saturation and the concentration C1 of oxygenated hemoglobin.

$$C2 = k(SaO2)C1$$

where k is a coefficient derived by calibration curves from experimental studies in human volunteers plotting known oxygen saturations at known concentrations of oxygenated hemoglobin against known concentrations of deoxyhemoglobin as determined by laboratory spectrophotometry
Thus $$Total\ Hb = C1 + KSaO2C1$$

As derived previously $$C1 = @PA/E940Ln940$$

where PA=pulsatile absorbance
C1=concentration of oxygenated hemoglobin
@=scalar coefficient
En=extinction coefficient at wavelength 940 nm (selected for oxygenated hemoglobin)
Ln=pathlength of light at wavelength 940 nm
Therefore $$Total\ Hb = @PA/E940Ln940 + KSaO2@PA/E940L940$$

I claim:

1. A process to determine continuously, non-invasively a hemoglobin concentration and hematocrit by analysis of a pulsatile component of absorbance of an isobestic wavelength of light for oxygenated hemoglobin and deoxyhemoglobin comprising the following steps:
   a. attaching a pressure cuff to an extremity of a patient;
   b. attaching a sensor probe from an isobestic wavelength oximeter to the extremity of said patient;
   c. inflating said pressure cuff above systolic arterial pressure, then deflating to determine systolic pressure;
   d. repeating steps a–c to determine the maximum systolic arterial pressure;
   d. determining the maximal arterial diameter from the maximum systolic arterial pressure;
   e. transmitting light at a predetermined isobestic wavelength from said sensor probe across said extremity such that the light passes through both venous blood, pulsatile arterial blood, and a tissue bed in said extremity;
   f. receiving light from said sensor probe that has passed through the extremity;
   g. determining the AC and DC components of the received light, AC and DC;
   h. determining said pulsatile component of absorbance PA of the received light which is related to the hemoglobin concentration and independent of the intensity of the received light from the formula PC=AC/DC;
   i. determining the hemoglobin concentration THB using the equation:

$$THB = @PA/E*Ln;$$

where @ is a scalar coefficient
   E is the extinction coefficient for light at the predetermined wavelength
   Ln is the path length of light at the predetermined wavelength; and
   j. determining hematocrit from THB.

2. A process to determine continuously, non-invasively a hemoglobin concentration and hematocrit by analysis of a pulsatile component of absorbance of an isobestic wavelength of light for oxygenated hemoglobin and deoxyhemoglobin comprising the following steps:
   a. attaching an ultrasonic echo tracking device to an extremity of a patient to allow continuous, non-invasive measurement of arterial diameter;
   b. attaching a sensor probe from an isobestic wavelength oximeter to said extremity of said patient;
   c. generating and detecting ultrasonic pulse with said ultrasonic echo tracking device;
   d. determining the maximal arterial diameter from the detected ultrasonic pulses;
   e. transmitting light of a predetermined isobestic wavelength from said sensor probe across said extremity such that the light passes through both venous blood, pulsatile arterial blood, and a tissue bed in said extremity;
   f. receiving light at said predetermined wavelength that has passed through the extremity using said sensor probe;
   g. determining the AC and DC components of the received light, AC and DC;
   h. determining said pulsatile component of absorbance PA of the received light which is related to the hemoglobin concentration and independent of the intensity of the received light from the formula PC=AC/DC;
   i. determining the hemoglobin concentration THB using the equation:

$$THB = @PA/E*Ln;$$

where @ is a scalar coefficient
   E is the extinction coefficient for light at the predetermined wavelength
   Ln is the path length of light at the predetermined wavelength; and
   j. determining hematocrit from THB.

* * * * *